(12) United States Patent
Dogra et al.

(10) Patent No.: US 9,269,909 B2
(45) Date of Patent: Feb. 23, 2016

(54) ELECTROACTIVE MATERIAL AND DEVICES MADE WITH SUCH MATERIALS

(75) Inventors: Kalindi Dogra, Wilmington, DE (US); Adam Fennimore, Wilmington, DE (US); Christina M Older, Wilmington, DE (US); Robert A. Eakin, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 320 days.

(21) Appl. No.: 13/989,296
(22) PCT Filed: Dec. 12, 2011
(86) PCT No.: PCT/US2011/064360
§ 371 (c)(1),
(2), (4) Date: May 23, 2013
(87) PCT Pub. No.: WO2012/082593
PCT Pub. Date: Jun. 21, 2012

(65) Prior Publication Data
US 2013/0240866 A1 Sep. 19, 2013

Related U.S. Application Data

(60) Provisional application No. 61/423,372, filed on Dec. 15, 2010.

(51) Int. Cl.
*H01L 51/50* (2006.01)
*H01L 51/00* (2006.01)
(Continued)

(52) U.S. Cl.
CPC .......... *H01L 51/0072* (2013.01); *C07D 471/04* (2013.01); *C09K 11/06* (2013.01); *H01L 51/0558* (2013.01); *H01L 51/5072* (2013.01); *H05B 33/20* (2013.01)

(58) Field of Classification Search
CPC .............. C07D 471/04; H01L 51/0072; H01L 51/0558; H01L 51/5072; H05B 33/20; H05B 33/34; C09K 11/06
See application file for complete search history.

(56) References Cited

U.S. PATENT DOCUMENTS
6,670,645 B2   12/2003   Grushin et al.
6,875,524 B2   4/2005    Hatwar et al.
(Continued)

FOREIGN PATENT DOCUMENTS
WO   03040257 A1   5/2003
WO   03063555 A1   7/2003
(Continued)

OTHER PUBLICATIONS

CRC Handbook of Chemistry and Physics, 81st Edition, 2000 (Book Not Included).
(Continued)

*Primary Examiner* — Dawn L. Garrett

(57) ABSTRACT

There is provided a compound having Formula I or Formula II

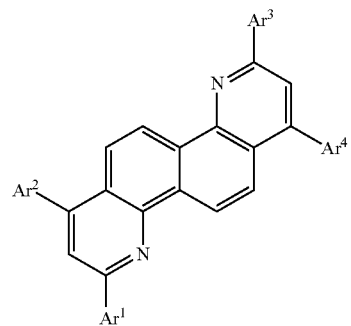

Formula I

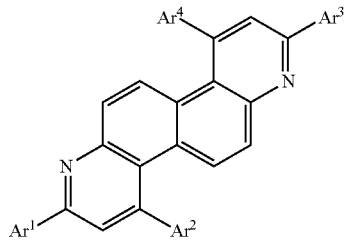

Formula II where:
$Ar^1$-$Ar^4$ are the same or different and are H, D, or aryl.

15 Claims, 3 Drawing Sheets

(51) Int. Cl.
| | |
|---|---|
| *C09K 11/06* | (2006.01) |
| *C07D 471/04* | (2006.01) |
| *H01L 51/05* | (2006.01) |
| *H05B 33/20* | (2006.01) |

(56) References Cited

U.S. PATENT DOCUMENTS

| | | | |
|---|---|---|---|
| 8,569,751 B2 * | 10/2013 | Horiuchi et al. | 257/40 |
| 9,005,777 B2 * | 4/2015 | Jung et al. | 428/690 |
| 2004/0102577 A1 | 5/2004 | Hsu et al. | |
| 2004/0127637 A1 | 7/2004 | Hsu et al. | |
| 2005/0158577 A1 | 7/2005 | Ishibashi et al. | |
| 2005/0205860 A1 | 9/2005 | Hsu et al. | |
| 2007/0063638 A1 | 3/2007 | Tokairin et al. | |
| 2007/0088185 A1 | 4/2007 | Kubota et al. | |
| 2007/0292713 A9 | 12/2007 | Dobbs et al. | |
| 2011/0037381 A1 * | 2/2011 | Rostovtsev et al. | 313/504 |

FOREIGN PATENT DOCUMENTS

| | | |
|---|---|---|
| WO | 2004016710 A1 | 2/2004 |
| WO | 2007021117 A1 | 2/2007 |
| WO | 2009018009 A1 | 2/2009 |
| WO | 2009067419 A1 | 5/2009 |
| WO | 2010035364 A1 | 4/2010 |
| WO | 2010135403 A2 | 11/2010 |
| WO | 2011021545 A1 | 2/2011 |
| WO | 2011024391 A1 | 3/2011 |

OTHER PUBLICATIONS

Wang—Photoconductive Materials, Kirk-Othmer Encyclopedia of Chemical Technology, Fourth Edition, 1996, vol. 18 pp. 837-860.
Sze, S.M., Physics of Semiconductor Devices, 2nd Edition,1981, John Wiley & Sons, p. 492.
Gustafsson et al., "Flexible Light-Emitting Diodes Made from Soluble Conducting Polymers," Nature, 1992, vol. 357, pp. 477-479.
Markus et al., Electronics and Nucleonics Dictionary, pp. 470-471 & 476 (McGraw-Hill 1966).
Cyranski et al., Separation of the Energetic and Geometric Contributions to the Aromaticity, Tetrahedron, 1996, vol. 52, No. 43, pp. 13795-13802.
Whaley et al., Nitrogen Isologs of Chrysene, Journal of Organic Chemistry, 1954, pp. 661-665.
Nekrasov et al., Polynuclear Azaaromatic Compounds, vol. 7, 1971, pp. 186-195.
ISR 20121106; PCT International Search Report for Application No. PCT/US2011/064360, counterpart to U.S. Appl. No. 13/989,296; Traegler-Goeldel, M., Authorized Officer; Nov. 6, 2012.

* cited by examiner

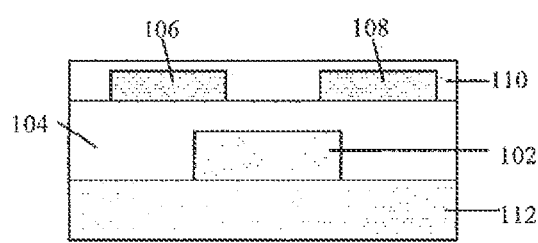
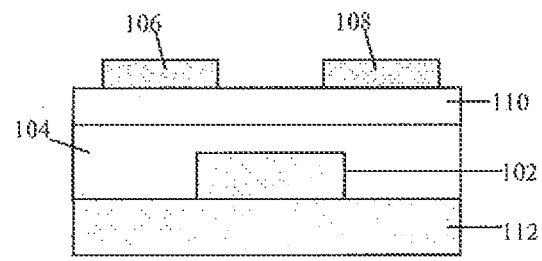
FIG. 1A    FIG. 1B
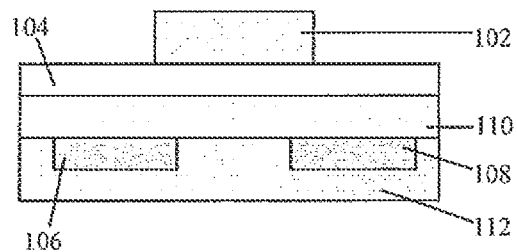
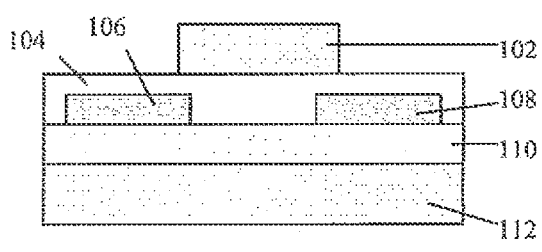
FIG. 1C    FIG. 1D

ELECTROACTIVE MATERIAL AND DEVICES MADE WITH SUCH MATERIALS

RELATED APPLICATION DATA

This application claims priority under 35 U.S.C. §119(e) from U.S. Provisional Application No. 61/423,372, filed on Dec. 15, 2010, which is incorporated by reference herein in its entirety.

BACKGROUND INFORMATION

1. Field of the Disclosure

This disclosure relates in general to electroactive compounds. It also relates to organic electronic devices including at least one layer having the electroactive compound.

2. Description of the Related Art

In organic photoactive electronic devices, such as organic light emitting diodes ("OLED"), that make up OLED displays, the organic active layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for new materials for electronic devices.

SUMMARY

There is provided a compound having Formula I or Formula II

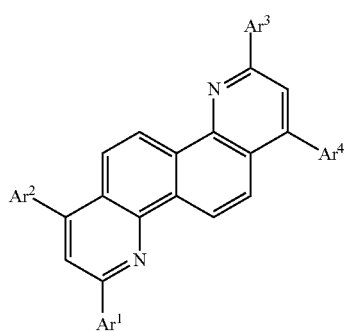

Formula I

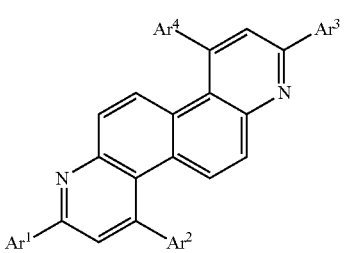

Formula II where:
Ar$^1$-Ar$^4$ are the same or different and are H, D, or aryl.

There is also provided a composition comprising (a) a host compound having Formula I or Formula II and (b) a dopant capable of electroluminescence having an emission maximum between 380 and 750 nm.

There is also provided an electronic device comprising at least one layer comprising the compound of Formula I or Formula II.

There is also provided a thin film transistor comprising:
a substrate
an insulating layer;
a gate electrode;
a source electrode;
a drain electrode; and
an organic semiconductor layer comprising an electroactive compound having Formula I or Formula II;
wherein the insulating layer, the gate electrode, the semiconductor layer, the source electrode and the drain electrode can be arranged in any sequence provided that the gate electrode and the semiconductor layer both contact the insulating layer, the source electrode and the drain electrode both contact the semiconductor layer and the electrodes are not in contact with each other.

There is also provided an electronic device comprising at least one active layer positioned between two electrical contact layers, wherein the at least one active layer of the device includes an electroactive compound having Formula II.

There is also provided an organic electronic device comprising an anode, a hole injection layer, a photoactive layer, an electron transport layer, and a cathode, wherein at least one of the photoactive layer and the electron transport layer comprises a compound having Formula I or Formula II.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 1A includes a schematic diagram of an organic field effect transistor (OTFT) showing the relative positions of the active layers of such a device in bottom contact mode.

FIG. 1B includes a schematic diagram of an OTFT showing the relative positions of the active layers of such a device in top contact mode.

FIG. 1C includes a schematic diagram of an organic field effect transistor (OTFT) showing the relative positions of the active layers of such a device in bottom contact mode with the gate at the top.

FIG. 1D includes a schematic diagram of an organic field effect transistor (OTFT) showing the relative positions of the active layers of such a device in bottom contact mode with the gate at the top.

Figure 2:
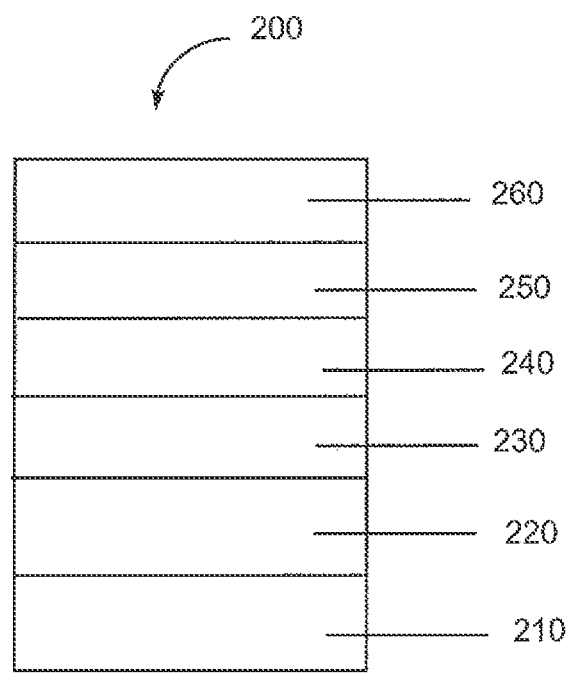
FIG. 2 includes a schematic diagram of another example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the New Compounds, the Electroactive Composition, the Electronic Device, and finally Examples.

1. Definitions and Clarification of Terms

Before addressing details of embodiments described below, some terms are defined or clarified.

The term "alkyl" is intended to mean a group derived from an aliphatic hydrocarbon.

The term "aryl" is intended to mean a group derived from an aromatic hydrocarbon. The term "aromatic compound" is intended to mean an organic compound comprising at least one unsaturated cyclic group having delocalized pi electrons. The term is intended to encompass both aromatic compounds having only carbon and hydrogen atoms, and heteroaromatic compounds wherein one or more of the carbon atoms within the cyclic group has been replaced by another atom, such as nitrogen, oxygen, sulfur, or the like.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although photoactive materials may also have some charge transport properties, the term "charge transport layer, material, member, or structure" is not intended to include a layer, material, member, or structure whose primary function is light emission or light reception.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "host material" is intended to mean a material, usually in the form of a layer, to which a dopant may or may not be added. The host material may or may not have electronic characteristic(s) or the ability to emit, receive, or filter radiation.

The term "hydrocarbon aryl" is intended to mean an aryl group containing only hydrogen and carbon atoms.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The term "N-heterocycle" is intended to mean a heteroaromatic group having at least one nitrogen in the aromatic ring.

The term "organic electronic device," or sometimes just "electronic device," is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector).

Unless otherwise indicated, all groups can be unsubstituted or substituted. Unless otherwise indicated, all groups can be linear, branched or cyclic, where possible. In some embodiments, the substituents are selected from the group consisting of alkyl, alkoxy, and aryl.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is citedIn case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. New Compounds

Electron transport materials have been used as host materials in photoactive layers and in electron transport layers. Electron transport materials based on metal complexes of quinoline ligands, such as with Al, Ga, or Zr, have been used in these applications. However, there are several disadvantages. The complexes can have poor atmospheric stability when used as hosts. It is difficult to plasma clean fabricated parts employing such metal complexes. The low triplet energy leads to quenching of phosphorescent emission of >2.0 eV energy. In some embodiments, the new compounds described herein have higher triplet energies.

In some embodiments, the new compounds are useful as solution processible electron dominated hosts for OLED devices or as electron transport materials suitable for n-doping in OLED devices having a thick electron transport layer. In some embodiments, devices made with the new compounds can have lower operating voltage, higher efficiency and longer lifetimes. In some embodiments, the materials are useful in any printed electronics application including photovoltaics and TFTs.

In some embodiments, the compound having Formula I or Formula II is deuterated. The term "deuterated" is intended to mean that at least one H has been replaced by D. The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage. In some embodiments, the compound is at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments, $Ar^1$-$Ar^4$ are the same or different and are selected from the group consisting of hydrocarbon aryls, N-heterocycles, and deuterated analogs thereof. In some embodiments, at least one of $Ar^1$-$Ar^4$ is substituted. Suitable substituents for such groups include, but are not limited to, alkyl, aryl, silyl, diarylamine, carbazole, or deuterated analogs thereof. In some embodiments, the aryl substituent is heteroaryl.

In some embodiments, $Ar^1$-$Ar^4$ are the same or different and all have Formula a

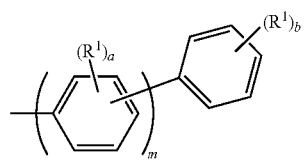

Formula a where:
$R^1$ is the same or different at each occurrence and is D, aryl, alkyl, silyl, diarylamino, carbazolyl, or a deuterated analog thereof;

a is the same or different at each occurrence and is an integer from 0-4;

b is an integer from 0-5; and m is an integer from 1 to 5.

In some embodiments, $Ar^1$-$Ar^4$ are the same or different and all have Formula b

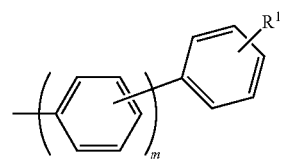

Formula b where $R^1$ and m are as defined above. The group with Formula b may also be deuterated.

In some embodiments, of Formula a and Formula b, m is 1-2.

In some embodiments. $Ar^1$-$Ar^4$ are the same or different and all have Formula c

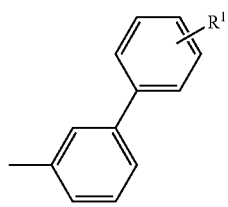

Formula c where $R^1$ is as defined above. The group with Formula c may also be deuterated.

In some embodiments, $Ar^1$-$Ar^4$ are the same or different and have a formula selected from the group consisting of Formula a, Formula b, and Formula c, as defined above.

In some embodiments, one or more of $Ar^1$-$Ar^4$ is phenyl, biphenyl, terphenyl, naphthyl, phenylnaphthyl, naphthylphenyl, pyridine, pyridimine, triazine, or a deuterated analog thereof. In some embodiments, at least one of $Ar^1$-$Ar^4$ is substituted with diarylamino, carbazole, or a deuterated analog thereof.

In some embodiments, $Ar^1$=$Ar^3$ and is different from $Ar^2$=$Ar^4$. In some embodiments, all of $Ar^1$-$Ar^4$ are the same.

Some examples of compounds having Formula I are shown below.

Compound 1
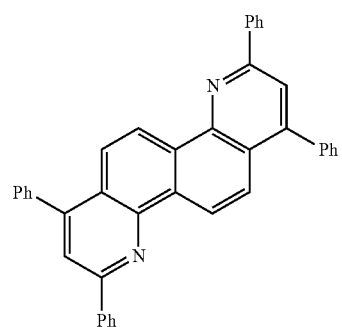
Compound 2
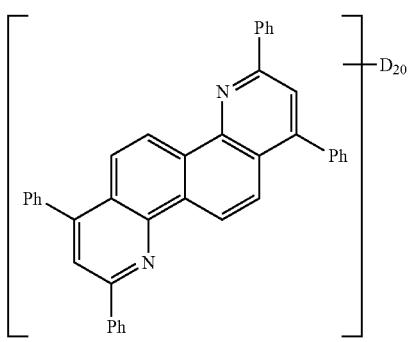
Compound 3
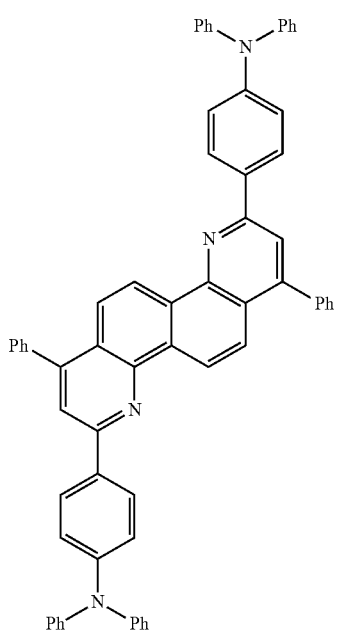
Compound 4
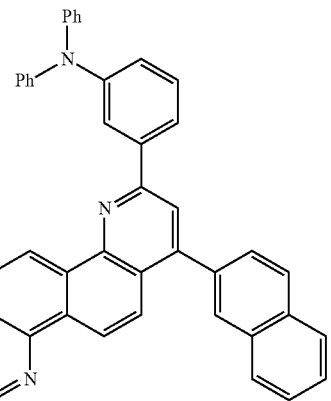
Compound 5
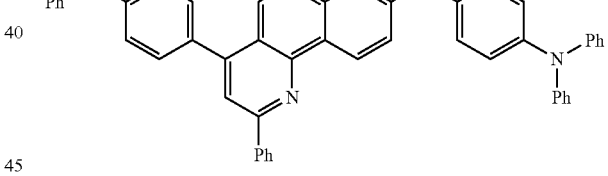
Some examples of compounds having Formula I are shown below.
Compound 6
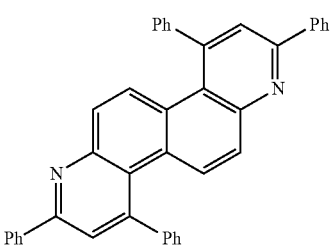

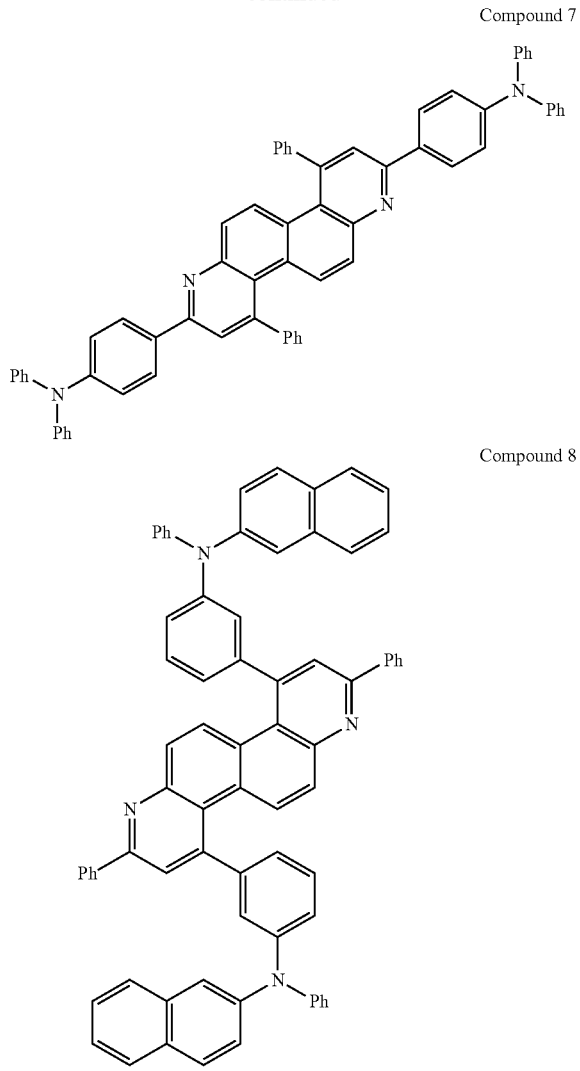

Compound 7

Compound 8

In the above structures, "Ph" represents a phenyl group.

The new compounds having Formulae I and H can be made by known synthetic techniques. The core tetracyclic diazachrysene structure is readily prepared via acid-mediated cyclization of enamine derivatives of 1,5- and 2,6-diaminonaphthalene. Chlorination (halogenation) and subsequent metal-catalyzed cross-coupling reactions leads to large variety of potential structures. It is also possible to generate this class of compounds via a double Skraup reaction on the diaminonaphthalenes. Other routes to this core structure can be easily devised by those skilled in the art. This is further illustrated in the examples.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCl, etc. Deuteration reactions have also been described in copending application [UC0917].

3. Electroactive Composition

There is also provided a composition comprising (a) a host compound having Formula I or Formula II and (b) a dopant capable of electroluminescence having an emission maximum between 380 and 750 nm. The new compounds of Formulae I and H are useful as host materials for photoactive materials. The compounds can be used alone, or in combination with another host material. The compounds of Formulae I and H can be used as a host for dopants with any color of emission. In some embodiments, the compound as used as hosts for organometallic electroluminescent material.

In some embodiments, the composition comprises (a) a host compound having Formula I or Formula II and (b) a photoactive dopant capable of electroluminescence having an emission maximum between 380 and 750 nm. In some embodiments, the composition consists essentially of (a) a host compound having Formula I or Formula II and (b) a photoactive dopant capable of electroluminescence having an emission maximum between 380 and 750 nm. In some embodiments, the composition comprises (a) a host compound having Formula I or Formula II, (h) a photoactive dopant capable of electroluminescence having an emission maximum between 380 and 750 nm, and (c) a second host material. In some embodiments, the composition comprises (a) a host compound having Formula I or Formula II, (b) a photoactive dopant capable of electroluminescence having an emission maximum between 380 and 750 nm, and (c) a second host material.

The amount of dopant present in the composition is generally in the range of 3-20% by weight, based on the total weight of the composition; in some embodiments, 5-15% by weight. When a second host is present, the ratio of first host having Formula I to second host is generally in the range of 1:20 to 20:1; in some embodiments, 5:15 to 15:5. In some embodiments, the first host material having Formula I is at least 50% by weight of the total host material; in some embodiments, at least 70% by weight.

Electroluminescent ("EL") materials which can be used as a dopant include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, derivatives thereof, and mixtures thereof. Examples of metal complexes include, but are not limited to, metal chelated oxinoid compounds and cyclometallated complexes of metals such as iridium and platinum. Examples of conjugated polymers include, but are not limited to poly(phenylenevinylenes), polyfluorenes, poly(spirobifluorenes), polythiophenes, poly (p-phenylenes), copolymers thereof, and mixtures thereof.

Examples of red light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published U.S. application 2005-0158577.

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published POT application WO 2007/021117.

Examples of blue light-emitting materials include, but are not limited to, complexes of Ir having phenylpyridine or phenylimidazole ligands, diarylanthracenes, diaminochrysenes, diaminopyrenes, and polyfluorene polymers. Blue light-emitting materials have been disclosed in, for example, U.S. Pat. No. 6,875,524, and published U.S. applications 2007-0292713 and 2007-0063638, In some embodiments, the dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral and is a tris-cyclometallated complex of iridium having the formula $IrL_3$ or a bis-cyclometallated complex of iridium having the formula $IrL_2Y$. In some embodiments. L is a monoanionic bidentate cyclometalating ligand coordinated through a carbon atom and a nitrogen atom. In some embodiments. L is an aryl N-heterocycle, where the aryl is phenyl or napthyl, and the N-heterocycle is pyridine, quinoline, isoquinoline, diazine, pyrrole, pyrazole or imidazole. In some embodiments, Y is a monoanionic bidentate ligand. In some embodiments, L is a phenylpyridine, a phenylquinoline, or a phenylisoquinoline. In some embodiments, Y is a β-dienolate, a diketimine, a picolinate, or an N-alkoxypyrazole. The ligands may be unsubstituted or substituted with F, D, alkyl, perfluororalkyl, alkoxyl, alkylamino, arylamino, CN, silyl, fluoroalkoxyl or aryl groups. In some embodiments, the dopant is a cyclometalated complex of iridium or platinum. Such materials have been disclosed in, for example, U.S. Pat. No. 6,670,645 and Published POT Applications WO 03/063555, WO 2004/016710, and WO 03/040257.

In some embodiments, the dopant is a complex having the formula $Ir(L1)_a(L2)_b(L3)_c$; where L1 is a monoanionic bidentate cyclometalating ligand coordinated through carbon and nitrogen;

L2 is a monoanionic bidentate ligand which is not coordinated through a carbon;

L3 is a monodentate ligand;

a is 1-3;

b and c are independently 0-2; and a, b, and c are selected such that the iridium is hexacoordinate and the complex is electrically neutral.

Some examples of formulae include, but are not limited to, $Ir(L1)_3$; $Ir(L1)_2(L2)$; and $Ir(L1)_2(L3)(L3')$, where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanoles (phosphinoalkoxide ligands).

Monodentate ligand L3 can be anionic or nonionic. Anionic ligands include, but are not limited to, H— ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls. The iridium complex dopants can be made using standard synthetic techniques as described in, for example, U.S. Pat. No. 6,670,645.

In some embodiments, the dopant is a small organic luminescent compound. In some embodiments, the dopant is selected from the group consisting of a non-polymeric spirobifluorene compound and a fluoranthene compound.

In some embodiments, the dopant is a compound having aryl amine groups. In some embodiments, the photoactive dopant is selected from the formulae below:

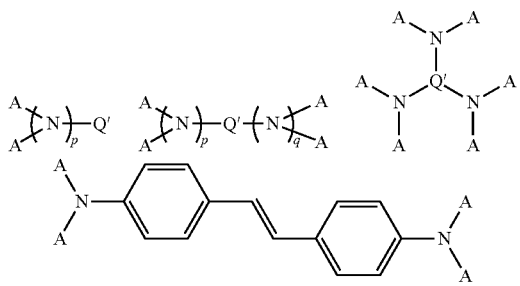

where:

A is the same or different at each occurrence and is an aromatic group having from 3-60 carbon atoms;

Q is a single bond or an aromatic group having from 3-60 carbon atoms;

p and q are independently an integer from 1-6.

In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

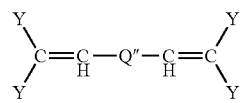

where:

Y is the same or different at each occurrence and is an aromatic group having 3-60 carbon atoms:

Q" is an aromatic group, a divalent triphenylamine residue group, or a single bond.

In some embodiments, the dopant is an aryl acene. In some embodiments, the dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the new compound is used with an additional host material. In some embodiments, the new compound is not used as a host in the photoactive layer. Examples of other types of hosts which can be used alone or in combination with the new compounds, include, but are not limited to, indolocarbazoles, chrysenes, phenanthrenes, triphenylenes, phenanthrolines, triazines, naphthalenes, anthracenes, quinolines, isoquinolines, quinoxalines, phenylpyridines, benzodifurans, and metal quinolinate complexes, and deuterated analogs thereof.

4. Organic Electronic Device

Organic electronic devices that may benefit from having one or more layers comprising the deuterated materials described herein include, but are not limited to, (1) devices that convert electrical energy into radiation (e.g., a light-emitting diode, light-emitting diode display, light-emitting luminaire, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a thin film transistor or diode). The compounds of the invention often can be useful in applications such as oxygen sensitive indicators and as luminescent indicators in bioassays.

In one embodiment, an organic electronic device comprises at least one layer comprising the compound having Formula I as discussed above.

a. First Exemplary Device

A particularly useful type of transistor, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices. $2^{nd}$ edition, John Wiley and Sons, page 492). These components can be assembled in a variety of configurations. An organic thin-film transistor (OTFT) is characterized by having an organic semiconductor layer.

In one embodiment, an OTFT comprises:
  a substrate
  an insulating layer;
  a gate electrode;
  a source electrode;
  a drain electrode; and
  an organic semiconductor layer comprising an electroactive compound having Formula I or Formula II;
wherein the insulating layer, the gate electrode, the semiconductor layer, the source electrode and the drain electrode can be arranged in any sequence provided that the gate electrode and the semiconductor layer both contact the insulating layer, the source electrode and the drain electrode both contact the semiconductor layer and the electrodes are not in contact with each other.

In FIG. 1A, there is schematically illustrated an organic field effect transistor (OTFT) showing the relative positions of the active layers of such a device in "bottom contact mode." (In "bottom contact mode" of an OTFT, the drain and source electrodes are deposited onto the gate dielectric layer prior to depositing the active organic semiconductor layer onto the source and drain electrodes and any remaining exposed gate dielectric layer.) A substrate 112 is in contact with a gate electrode 102 and an insulating layer 104 on top of which the source electrode 106 and drain electrode 108 are deposited. Over and between the source and drain electrodes are an organic semiconductor layer 110 comprising an electroactive compound of Formula I or Formula II.

FIG. 1B is a schematic diagram of an OTFT showing the relative positions of the active layers of such a device in top contact mode, (In "top contact mode," the drain and source electrodes of an OTFT are deposited on top of the active organic semiconductor layer.)

FIG. 1C is a schematic diagram of OTFT showing the relative positions of the active layers of such a device in bottom contact mode with the gate at the top.

FIG. 1D is a schematic diagram of an OTFT showing the relative positions of the active layers of such a device in top contact mode with the gate at the top.

The substrate can comprise inorganic glasses, ceramic foils, polymeric materials (for example, acrylics, epoxies, polyamides, polycarbonates, polyimides, polyketones, poly (oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and/or coated metallic foils. The thickness of the substrate can be from about 10 micrometers to over 10 millimeters; for example, from about 50 to about 100 micrometers for a flexible plastic substrate; and from about 1 to about 10 millimeters for a rigid substrate such as glass or silicon. Typically, a substrate supports the OTFT during manufacturing, testing, and/or use. Optionally, the substrate can provide an electrical function such as bus line connection to the source, drain, and electrodes and the circuits for the OTFT.

The gate electrode can be a thin metal film, a conducting polymer film, a conducting film made from conducting ink or paste or the substrate itself, for example heavily doped silicon. Examples of suitable gate electrode materials include aluminum, gold, chromium, indium tin oxide, conducting polymers such as polystyrene sulfonate-doped poly(3,4-ethylenedioxythiophene) (PSS-PEDOT), conducting ink/paste comprised of carbon black/graphite or colloidal silver dispersion in polymer binders. In some OTFTs, the same material can provide the gate electrode function and also provide the support function of the substrate. For example, doped silicon can function as the gate electrode and support the OTFT.

The gate electrode can be prepared by vacuum evaporation, sputtering of metals or conductive metal oxides, coating from conducting polymer solutions or conducting inks by spin coating, casting or printing. The thickness of the gate electrode can be, for example, from about 10 to about 200 nanometers for metal films and from about 1 to about 10 micrometers for polymer conductors.

The source and drain electrodes can be fabricated from materials that provide a low resistance ohmic contact to the semiconductor layer, such that the resistance of the contact between the semiconductor layer and the source and drain electrodes is less than the resistance of the semiconductor layer. Channel resistance is the conductivity of the semiconductor layer. Typically, the resistance should be less than the channel resistance. Typical materials suitable for use as source and drain electrodes include aluminum, barium, calcium, chromium, gold, silver, nickel, palladium, platinum, titanium, and alloys thereof; carbon nanotubes; conducting polymers such as polyaniline and poly(3,4-ethylenedioxythiophene)/poly-(styrene sulfonate) (PEDOT:PSS); dispersions of carbon nanotubes in conducting polymers; dispersions of a metal in a conducting polymer; and multilayers thereof. Some of these materials are appropriate for use with n-type semiconductor materials and others are appropriate for use with p-type semiconductor materials, as is known to those skilled in the art. Typical thicknesses of source and drain electrodes are about, for example, from about 40 nanometers to about 1 micrometer. In some embodiments, the thickness is about 100 to about 400 nanometers.

The insulating layer comprises an inorganic material film or an organic polymer film. Illustrative examples of inorganic materials suitable as the insulating layer include aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of the aforesaid materials can be used for the insulating layer. Illustrative examples of organic polymers for the insulating layer include polyesters, polycarbonates, poly(vinyl phenol), polyimides, polystyrene, poly(methacrylate)s, poly(acrylate)s, epoxy resins and blends and multilayers thereof. The thickness of the insulating layer is, for example from about 10 nanometers to about 500 nanometers, depending on the dielectric constant of the dielectric material used. For example, the thickness of the insulating layer can be from about 100 nanometers to about 500 nanometers. The insulating layer can have a conductivity that is, for example, less than about $10^{-12}$ S/cm (where S=Siemens=1/ohm).

The insulating layer, the gate electrode, the semiconductor layer, the source electrode, and the drain electrode are formed in any sequence as long as the gate electrode and the semiconductor layer both contact the insulating layer, and the source electrode and the drain electrode both contact the semiconductor layer. The phrase "in any sequence" includes sequential and simultaneous formation. For example, the source electrode and the drain electrode can be formed simultaneously or sequentially. The gate electrode, the source electrode, and the drain electrode can be provided using known methods such as physical vapor deposition (for example, thermal evaporation or sputtering) or ink jet printing. The patterning of the electrodes can be accomplished by known methods such as shadow masking, additive photolithography, subtractive photolithography, printing, microcontact printing, and pattern coating.

For the bottom contact mode OTFT (FIG. 1A), electrodes 106 and 108, which form channels for source and drain respectively, can be created on the silicon dioxide layer using a photolithographic process. A semiconductor layer 110 is then deposited over the surface of electrodes 106 and 108 and layer 104.

In one embodiment, semiconductor layer 110 comprises one or more compounds represented by Formula I or Formula II. The semiconductor layer 110 can be deposited by various techniques known in the art. These techniques include thermal evaporation, chemical vapor deposition, thermal transfer, ink-jet printing and screen-printing. Dispersion thin film coating techniques for deposition include spin coating, doctor blade coating, drop casting and other known techniques.

For top contact mode OTFT (FIG. 1B), layer 110 is deposited on layer 104 before the fabrication of electrodes 106 and 108.

b. Second Exemplary Device

The present invention also relates to an electronic device comprising at least one active layer positioned between two electrical contact layers, wherein the at least one active layer of the device includes a new compound having Formula I or Formula II.

Another example of an organic electronic device structure is shown in FIG. 2. The device 200 has a first electrical contact layer, an anode layer 210 and a second electrical contact layer, a cathode layer 260, and a photoactive layer 240 between them. Adjacent to the anode may be a hole injection layer 220. Adjacent to the hole injection layer may be a hole transport layer 230, comprising hole transport material. Adjacent to the cathode may be an electron transport layer 250, comprising an electron transport material. Devices may use one or more additional hole injection or hole transport layers (not shown) next to the anode 210 and/or one or more additional electron injection or electron transport layers (not shown) next to the cathode 260.

Layers 220 through 250 are individually and collectively referred to as the active layers.

Figure 3:
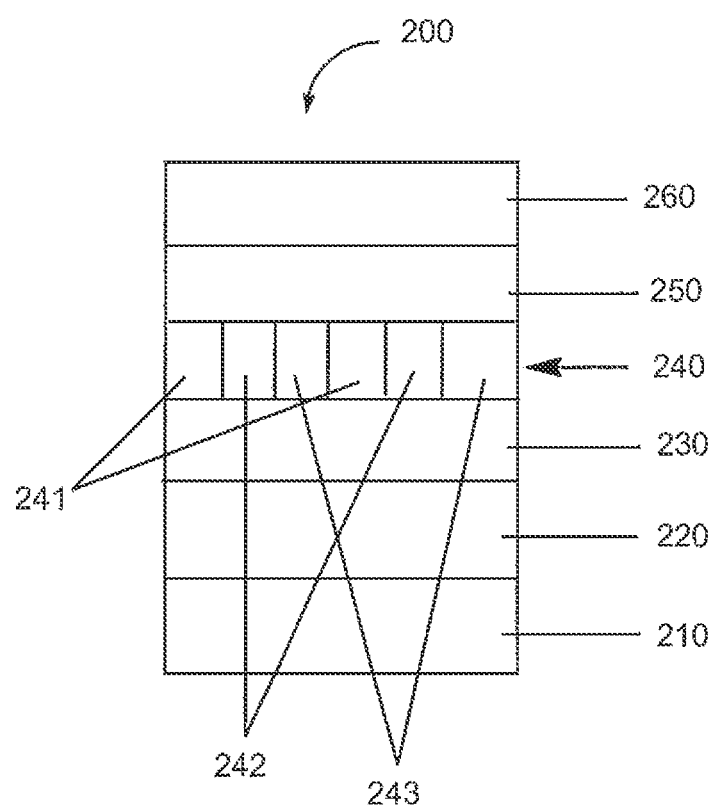
FIG. 3 includes a schematic diagram of another example of an organic electronic device.

In some embodiments, the photoactive layer 240 is pixelated, as shown in FIG. 3. Layer 240 is divided into pixel or subpixel units 241, 242, and 243 which are repeated over the layer. Each of the pixel or subpixel units represents a different color. In some embodiments, the subpixel units are for red, green, and blue. Although three subpixel units are shown in the figure, two or more than three may be used.

In one embodiment, the different layers have the following range of thicknesses: anode 210, 500-5000 Å, in one embodiment 1000-2000 Å; hole injection layer 220, 50-2000 Å, in one embodiment 200-1000 Å; hole transport layer 230, 50-2000 Å, in one embodiment 200-1000 Å; electroactive layer 240, 10-2000 Å, in one embodiment 100-1000 Å; layer 250, 50-2000 Å, in one embodiment 100-1000 Å; cathode 260, 200-10000 Å, in one embodiment 300-5000 Å. The location of the electron-hole recombination zone in the device, and thus the emission spectrum of the device, can be affected by the relative thickness of each layer. The desired ratio of layer thicknesses will depend on the exact nature of the materials used. In some embodiments, the devices have additional layers to aid in processing or to improve functionality.

Depending upon the application of the device 200, the photoactive layer 240 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966). Devices with light-emitting layers may be used to form displays or for lighting applications, such as white light luminaires.

One or more of the new electroactive compounds described herein may be present in one or more of the active layers of a device.

In some embodiments, the new electroactive compounds having Formula I or Formula II are useful as host materials for photoactive dopant materials in photoactive layer 240. It has been found that when these compounds are used by themselves or in conjunction with other cohosts, they can provide improved efficiency and lifetime in OLED devices. It has been discovered through calculations that these compounds have high triplet energies and HOMO and LUMO levels appropriate for charge transport, making them excellent host materials for organometallic emitters.

In some embodiments, the new electroactive compounds are useful as electron transport materials in layer 250.

Photoactive Layer

In some embodiments, the photoactive layer 240 comprises the electroactive composition described above.

In some embodiments, the dopant is an organometallic material. In some embodiments, the organometallic material is a complex of Ir or Pt. In some embodiments, the organometallic material is a cyclometallated complex of Ir.

In some embodiments, the photoactive layer comprises (a) a host material having Formula I or Formula II and (b) one or more dopants. In some embodiments, the photoactive layer comprises (a) a host material having Formula I or Formula II and (b) an organometallic electroluminescent dopant. In some embodiments, the photoactive layer comprises (a) a host material having Formula I or Formula II, (b) photoactive dopant, and (c) a second host material. In some embodiments, the photoactive layer comprises (a) a host material having Formula I or Formula II, (b) an organometallic complex of Ir or Pt, and (c) a second host material. In some embodiments, the photoactive layer comprises (a) a host material having Formula I or Formula II, (b) a cyclometallated complex of Ir, and (c) a second host material.

In some embodiments, the photoactive layer consists essentially of (a) a host material having Formula I or Formula II and (b) one or more dopants. In some embodiments, the photoactive layer consists essentially of (a) a host material having Formula I or Formula II and (b) an organometallic electroluminescent dopant. In some embodiments, the photoactive layer consists essentially of (a) a host material having Formula I or Formula II, (b) a photoactive dopant, and (c) a second host material. In some embodiments, the photoactive layer consists essentially of (a) a host material having Formula I or Formula II, (b) an organometallic complex of Ir or Pt, and (c) a second host material. In some embodiments, the photoactive layer consists essentially of (a) a host material having Formula I or Formula II, (b) a cyclometallated complex of Ir, and (c) a second host material.

In some embodiments, the photoactive layer consists essentially of (a) a host material having Formula I or Formula II, wherein the compound is deuterated, and (b) one or more dopants. In some embodiments, the photoactive layer consists essentially of a host material having Formula I or Formula II, wherein the compound is deuterated, and (b) an organometallic electroluminescent dopant. In some embodiments, the photoactive layer consists essentially of (a) a host material having Formula I or Formula II, wherein the compound is deuterated, (b) a photoactive dopant, and (c) a second host material. In some embodiments, the photoactive layer consists essentially of a host material having Formula I or Formula II, wherein the compound is deuterated, (b) an organometallic complex of Ir or Pt, and (c) a second host material. In some embodiments, the photoactive layer consists essentially of (a) a host material having Formula I or Formula II, wherein the compound is deuterated a host material having Formula I or Formula II, wherein the compound is deuterated, (b) a cyclometallated complex of Ir, and (c) a second host material. In some embodiments, the deuterated compound of Formula I or Formula II is at least 10% deuterated; in some embodiments, at least 50% deuterated. In some embodiments, the second host material is deuterated. In some embodiments, the second host material is at least 10% deuterated; in some embodiments, at least 50% deuterated.

Electron Transport Layer

The new compounds of Formulae I and II are useful as electron transport materials in layer 250. The compounds can be used alone, or in combination with another electron transport material. In some embodiments, the electron transport layer consists essentially of a new compound of Formula I or II.

Examples of other electron transport materials which can be used alone or in combination with the new compounds include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline: phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport material is selected from the group consisting of metal quinolates and phenanthroline derivatives. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

Other Device Layers

The other layers in the device can be made of any materials that are known to be useful in such layers.

The anode 210, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 210 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

The hole injection layer 220 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapour deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer. In some embodiments, the hole injection layer comprises an electrically conductive polymer doped with a fluorinated acid polymer. materials have been described in, for example, published U.S. patent applications U.S. 2004/0102577, U.S. 2004/0127637, U.S. 2005/0205860, and published PCT application WO 2009/018009.

Examples of hole transport materials for layer 230 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N'N-2,5-phenylenediamine (FDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

The cathode 260, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 210 and hole injection layer 220 to control the amount of positive charge injected and/or to provide bandgap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 210, active layers 220, 230, 240, and 250, or cathode layer 260, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

In some embodiments, the device is fabricated by liquid deposition of the buffer layer, the hole transport layer, and the photoactive layer, and by vapor deposition of the anode, the electron transport layer, an electron injection layer and the cathode.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials may also be considerations in selecting the electron and hole transport materials.

It is understood that the efficiency of devices made with the new compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The concepts described herein will be further described in the following examples, which do not limit the scope of the invention described in the claims.

Synthesis Example 1

This example illustrates the synthesis of Compound 1, 2, 4, 8, 10-tetraphenyl-quino[8,7-h]quinoline.

Step 1:

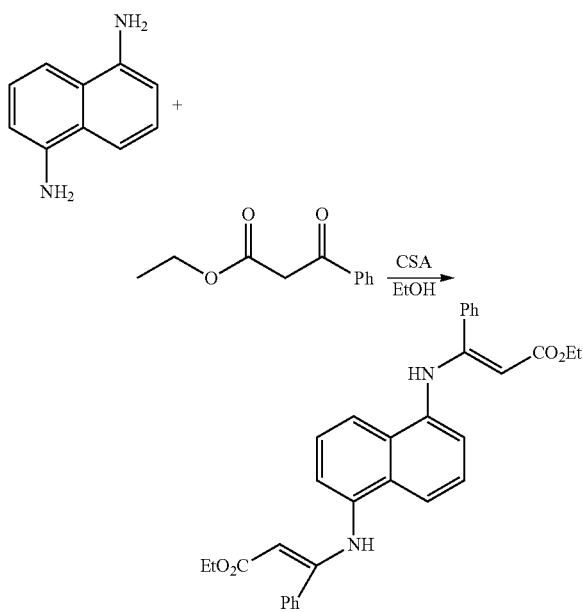

Combined 1,5-diaminonaphthalene (10.0 g, 63.1 mmol), ethyl benzoylacetate 22.8 mL, 133 mmol), and camphor-10-sulfonic acid (2.94 g, 12.6 mmol) and 400 mL anhydrous ethanol. The mixture was heated in the reaction flask at 90° C. and a Dean-Stark trap was used to drain 100 mL of solvent distillate over 5 hour period. The reaction was heated for a further 24 hrs. Afterwards 400 mL water was added to the cooled reaction mixture before filtering the precipitate, and the solids rinsed with methanol. The product was then recrystallized from hot toluene (1 L) and dried by vacuum to afford 23.9 g (74.5%) of white crystals.

Step 2:

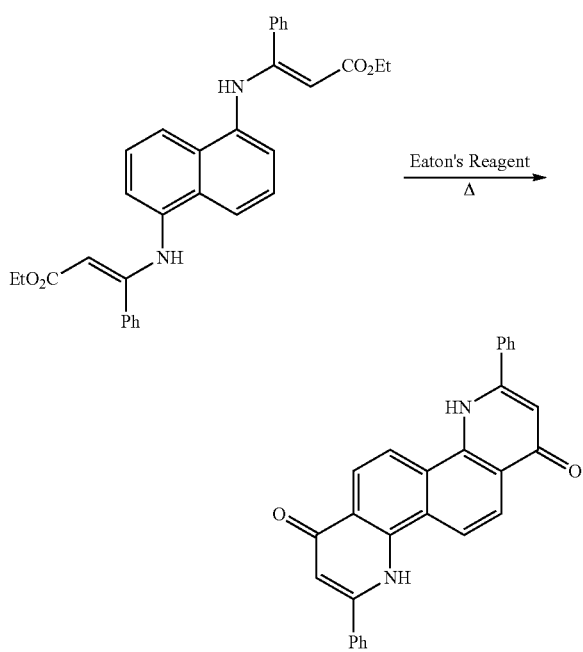

Eaton's Reagent (210 mL, 7.7 w % $P_2O_5$ in methanesulfonic acid) was freshly prepared prior to the reaction. Phosphorus pentoxide (24.06 g) and 195 mL methanesulfonic acid (288.44 g) were combined in the reaction flask under nitrogen and heated for 1 hour at 70° C. before cooling to room temperature. 1,5-Bis(ethyl benzoylacetanilide)naphthalene (23.5 g, 43.6 mmol) was added to the solution and the mixture heated to 50° C. under nitrogen for 34 hours before cooling to ambient temperature. Water (400 mL) was slowly added and the resulting mixture was then neutralized using 50% NaOH solution. This mixture was stirred for 1 hour before filtering, and the collected precipitate was rinsed with methanol before drying under vacuum to yield 18.55 g (96.5% yield) of an off-white powder.

Step 3:

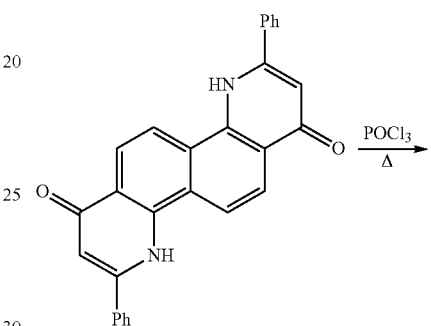

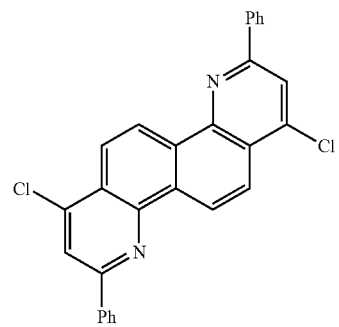

Phosphorus (V) oxychloride (165 mL) and substrate (18.5 g, 44.7 mmol) were combined in the reaction flask under nitrogen and warmed to reflux temperature for 7 hours before cooling back to room temperature. The mixture was slowly added to 4 L cold water and stirred for a further 30 minutes. The mixture was then neutralized with 50% NaOH solution. The precipitate was filtered and rinsed with 1 L water, followed by 500 mL methanol. The collected solid was dried under vacuum to yield 19.1 g of crude product. This material was then suspended in toluene and the slurry mixture warmed to reflux temperature with stirring. The solids never fully dissolved into the hot toluene. The mixture was allowed to come back to room temperature after 4 hours heating at reflux. The solids were then filtered and rinsed with toluene (500 mL) and hexanes (500 mL) and dried under vacuum to yield 18.3 g (90.8% yield). The structure was confirmed by $^1$H NMR using chlorobenzene-$d_5$ at 80° C.

Step 4:

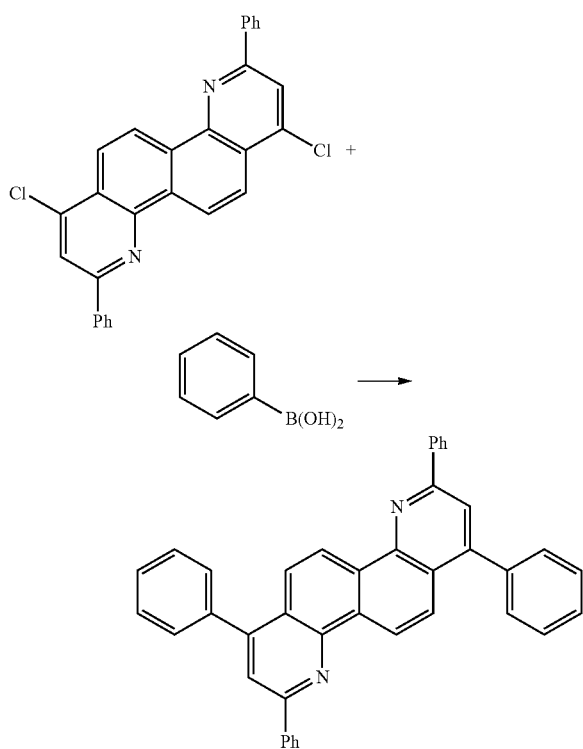

Phenylboronic acid (3.38 g, 27.7 mmol), 1,7-dichloro-4,10-diazachrysene (2.50 g, 5.50 mmol), potassium carbonate (19.1 g, 138 mmol) dissolved into 70 mL water, and 1,4-dioxane (70 mL) were combined in a flask and sparged with nitrogen for 45 minutes. Tris(dibenzilineacetone)dipalladium(0) (0.142 g, 0.140 mmol) and tricyclohosphine (0.112 g, 0.550 mmol) were combined under nitrogen atmosphere and this solution quickly added to the reaction mixture. The reaction mixture was heated at 90° C. for 20 hours. The reaction mixture was then cooled to room temperature and the product extracted with chloroform and the solution dried with magnesium sulfate before concentrating under reduced pressure. The crude product was then purified by column chromatography using silica gel and 100% chloroform as eluent. The product fractions were collected and concentrated under reduced pressure to afford an off-white solid. This residue was then recrystallized from hot toluene (~400 mL) to yield 1.82 g (61.6% yield). The product underwent vapor sublimation as a final purification step. The structure was confirmed by $^1$H NMR using chlorobenzene-$d_5$ at 80° C.

Device Example 1

This example illustrates the use of the new compounds in the electron transport layer of an OLED device.
(a) Device Materials and Structure
  anode=Indium Tin Oxide (ITO), 50 nm
  hole injection layer =HIJ-1, 50 nm. HIJ-1 is an aqueous dispersion of an electrically conductive polymer and a polymeric fluorinated sulfonic acid. Such materials have been described in, for example, published U.S. patent applications U.S. 2004/0102577, U.S. 2004/0127637, and U.S. 2005/0205860, and published PCT application WO 2009/018009.
  hole transport layer=HT-1 (20 nm). HT-1 is a hole transport material which is a triarylamine polymer. Such materials have been described in, for example, published PCT application WO 2009/067419.hole transport layer (HTL)=N,N'-bis(naphthalen-1-yl)-N,N'-bis-(phenyl)benzidine (NPB); 25 nm
  photoactive layer=host H1 with dopant E1 in a 1:13 weight ratio, 40 nm. H1 is a deuterated diarylanthracene. The non-deuterated analogs of such materials have been previously disclosed as blue host materials in, for example, published U.S. patent application no. U.S. 2007-0088185 (Idemitsu). E1 is a bis(diarylamino)chrysene. Such materials have been described in published PCT application WO2010035364.
  electron transport layer=the compound given below, 10 nm
  electron injection layer/cathode=CsF/Al, 1 nm/100 nm
  For Comparative Example A, the electron transport layer was tetrakis (8-hydroxyquinoline)zirconium ("ZrQ4").
  For Example 1, the electron transport layer was Compound 1.
(b) Device Fabrication
  OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.
  Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a toluene solution of HT-1, and then heated to remove solvent. The substrates were masked and placed in a vacuum chamber. After cooling the substrates were spin-coated with a methyl benzoate solution of the host and dopant, and heated to remove solvent.
  The substrates were masked and placed in a vacuum chamber. A layer of electron transport material was deposited by thermal evaporation, followed by a layer of CsF. Masks were then changed in vacuo and a layer of Al was deposited by thermal evaporation. The chamber was vented, and the devices were encapsulated using a glass lid, dessicant, and UV curable epoxy.
(c) Device Characterization
  The OLED samples were characterized by measuring their (1) current-voltage (1-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The color coordinates were determined using either a Minolta CS-100 meter or a Photoresearch PR-705 meter.

The results are given in Table 1.

TABLE 1

| Ex. | CIE (x, y) | Voltage (V) | C.E. (cd/A) | E.Q.E. (%) | P.E. (lm/W) | Projected Lifetime T50 |
|---|---|---|---|---|---|---|
| Comp. A-1 | 0.136, 0.131 | 4.8 | 5.8 | 5.4 | 3.8 | 19188 |
| Comp A-2 | 0.135, 0.133 | 4.8 | 6.0 | 5.6 | 3.9 | 23138 |
| Ex. 1-1 | 0.136, 0.127 | 4.7 | 6.0 | 5.8 | 4.0 | 22392 |
| Ex. 1-2 | 0.136, 0.128 | 4.6 | 6.3 | 6.0 | 4.3 | 24989 |

All data @ 1000 nits,

CE = current efficiency;

CIEx and CIEy are the x and y color coordinates according to the C.I.E. chromaticity scale (Commission Internationale de L'Eclairage, 1931).

Projected T50 is the time in hours for a device to reach one-half the initial luminance at 1000 nits, calculated using an acceleration factor of 1.7.

It can be seen that the device with the Compound 1 had equivalent or superior performance to the device with ZrQ4.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula I or Formula II

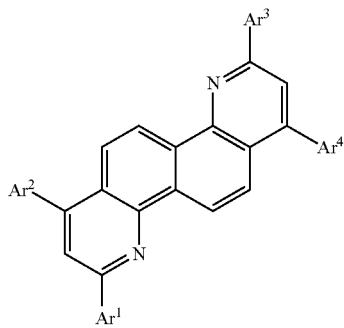

Formula I

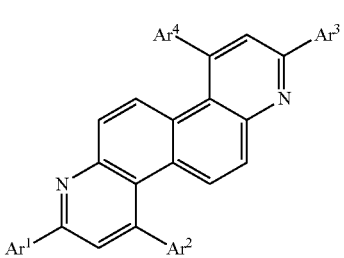

Formula II where:
Ar$^1$-Ar$^4$ are the same or different and are hydrocarbon aryls, N-heterocycles, or deuterated-analogs thereof.

2. The compound of claim 1, wherein at least one of Ar$^1$-Ar$^4$ has a substituent which is, alkyl, aryl, silyl, diarylamine, carbazole, or a deuterated analog thereof.

3. The compound of claim 1, wherein Ar$^1$-Ar$^4$ have Formula a

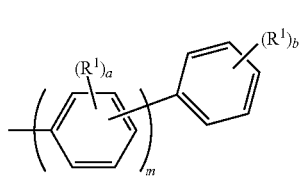

Formula a where:
R$^1$ is the same or different at each occurrence and is D, aryl, alkyl, silyl, diarylamino, carbazolyl, or a deuterated analog thereof;
a is the same or different at each occurrence and is an integer from 0-4;
b is an integer from 0-5; and
m is an integer from 1 to 5.

4. The compound of claim 1, wherein Ar$^1$-Ar$^4$ have Formula b

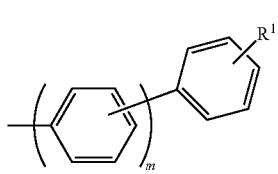

Formula b where:
 R[1] is H, D, aryl, alkyl, silyl, diarylamino, carbazolyl, or a deuterated analog thereof, and
 m is an integer from 1 to 5;
or a deuterated analog thereof.

5. The compound of claim 1, wherein Ar[1]-Ar[4] have Formula c

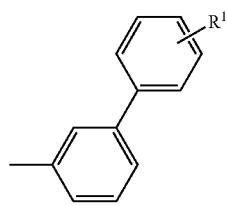

Formula c where
 R[1] is H, D, aryl, alkyl, silyl, diarylamino, carbazolyl, or a deuterated analog thereof, or a deuterated analog thereof.

6. The compound of claim 1, wherein one or more of Ar[1]-Ar[4] is phenyl, biphenyl, terphenyl, naphthyl, phenylnaphthyl, naphthylphenyl, pyridine, pyridimine, triazine, or a deuterated analog thereof.

7. The compound of claim 6, wherein at least one of Ar[1]-Ar[4] is substituted with diarylamino, carbazole, or a deuterated analog thereof.

8. A compound selected from Compound 1 through Compound 8:

Compound 1

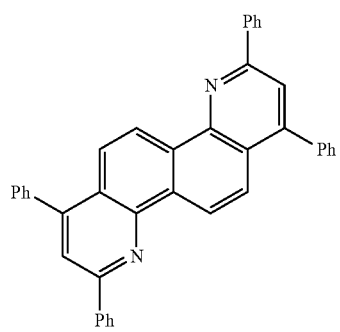

Compound 2

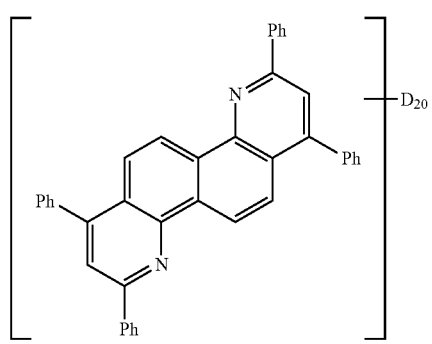

Compound 3

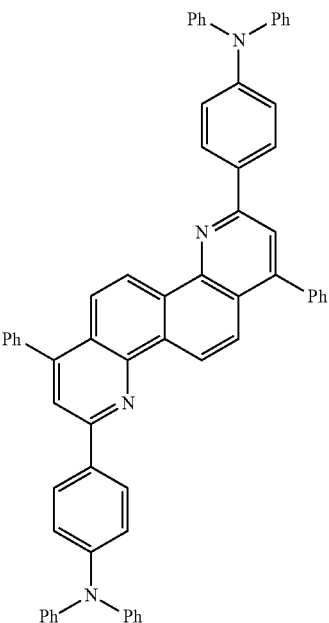

Compound 4

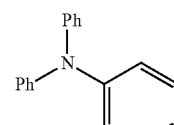
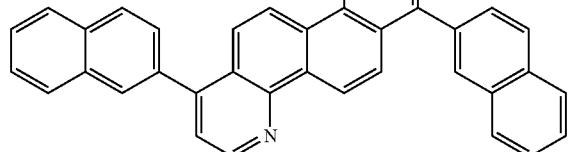
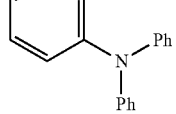

Compound 5

Compound 6

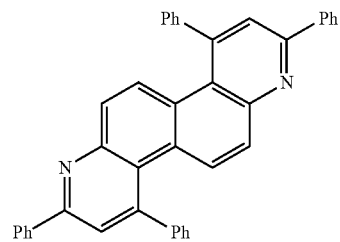

Compound 7

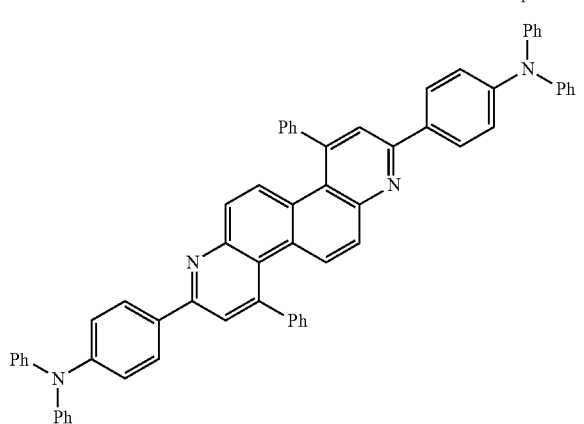

Compound 8

Formula I

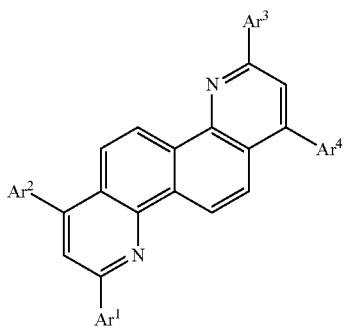

Formula II

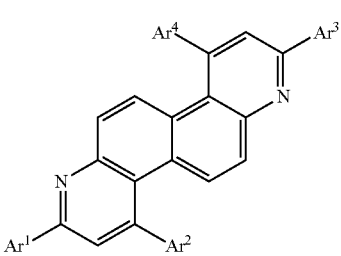

where:
Ar$^1$-Ar$^4$ are the same or different and are hydrocarbon aryls, N-heterocycles, or deuterated analogs thereof.

10. The device of claim 9, wherein the device is an organic thin-film transistor comprising:
   a substrate
   an insulating layer;
   a gate electrode;
   a source electrode;
   a drain electrode; and
   an organic semiconductor layer comprising an electroactive compound having Formula I or Formula II;
   wherein the insulating layer, the gate electrode, the semiconductor layer, the source electrode and the drain electrode can be arranged in any sequence provided that the gate electrode and the semiconductor layer both contact the insulating layer, the source electrode and the drain electrode both contact the semiconductor layer and the electrodes are not in contact with each other.

11. The device of claim 9, wherein the device comprises at least one active layer positioned between two electrical contact layers, wherein the at least one active layer of the device includes a compound having Formula I or Formula II.

12. The device of claim 11, comprising an anode, a hole injection layer, a photoactive layer, an electron transport layer, and a cathode, wherein at least one of the photoactive layer and the electron transport layer comprises a compound having Formula I or Formula II.

13. The device of claim 12, wherein the photoactive layer comprises (a) a host material having Formula I or Formula II and (b) an organometallic electroluminescent dopant.

14. The device of claim 13, wherein the hole injection layer comprises at least one electrically conductive polymer and at least one fluorinated acid polymer.

15. The device of claim 12, wherein the electron transport layer comprises a compound having Formula I or Formula II.

9. An electronic device having at least one layer comprising the compound of Formula I or Formula II

* * * * *